US010016371B2

(12) United States Patent
Keselowsky et al.

(10) Patent No.: US 10,016,371 B2
(45) Date of Patent: Jul. 10, 2018

(54) ANTIGEN-SPECIFIC, TOLERANCE-INDUCING MICROPARTICLES AND USES THEREOF

(75) Inventors: Benjamin George Keselowsky, Gainesville, FL (US); Jamal Lewis, Tallahassee, FL (US); Abhinav Acharya, Atlanta, GA (US); Michael J. Clare-Salzler, Gainesville, FL (US)

(73) Assignee: UNIVERSITY OF FLORIDA RESEARCH FOUNDATION, Gainesville, FL (US)

(*) Notice: Subject to any disclaimer, the term of this patent is extended or adjusted under 35 U.S.C. 154(b) by 676 days.

(21) Appl. No.: 13/880,778

(22) PCT Filed: Oct. 24, 2011

(86) PCT No.: PCT/US2011/057478
§ 371 (c)(1),
(2), (4) Date: Jul. 15, 2013

(87) PCT Pub. No.: WO2012/054920
PCT Pub. Date: Apr. 26, 2012

(65) Prior Publication Data
US 2013/0287729 A1    Oct. 31, 2013

Related U.S. Application Data

(60) Provisional application No. 61/405,999, filed on Oct. 22, 2010.

(51) Int. Cl.
| *A61K 39/00* | (2006.01) |
| *A61K 39/38* | (2006.01) |
| *A61K 45/00* | (2006.01) |
| *A61K 47/00* | (2006.01) |
| *A61K 9/50* | (2006.01) |
| *A61K 31/59* | (2006.01) |
| *A61K 47/69* | (2017.01) |

(52) U.S. Cl.
CPC ............ *A61K 9/5031* (2013.01); *A61K 31/59* (2013.01); *A61K 39/0008* (2013.01); *A61K 47/6937* (2017.08); *A61K 2039/55511* (2013.01); *A61K 2039/55522* (2013.01); *A61K 2039/6093* (2013.01); *A61K 2300/00* (2013.01)

(58) Field of Classification Search
None
See application file for complete search history.

(56) References Cited

U.S. PATENT DOCUMENTS

| 2005/0053667 A1 | 3/2005 | Irvine |
| 2006/0002852 A1 | 1/2006 | Saltzman |
| 2006/0078540 A1* | 4/2006 | Warren ............... C12N 5/0639 424/93.1 |
| 2010/0092425 A1 | 4/2010 | von Andrian et al. |

FOREIGN PATENT DOCUMENTS

| WO | WO 2005/013896 A2 | 2/2005 |
| WO | WO 2006/080951 A2 | 8/2006 |
| WO | WO 2009/051837 A2 | 4/2009 |
| WO | WO 2010/042866 A1 | 4/2010 |
| WO | WO 2010/042876 A1 | 4/2010 |

OTHER PUBLICATIONS

Zhao et al., 2005, Biomaterials, vol. 26: 5048-5063.*
Fu et al., 2010, Immunol. Res. vol. 46: 72-78.*
Di Rosa et al., 2011, Immunology, vol. 134: 123-139.*
Jhunjhunwala et al., Feb. 2009, J. Control. Release, vol. 133: 191-197.*
Gamvrellis et al., 2004, Imm. Cell. Biol. vol. 82: 506-516*
Champion et al., 2008, PHarm. Res. vol. 25: 1815-1821.*
Segura et al., 2007, Antmicro. agents and chem. vol. 51: 1310-1314.*
Meraz et al., 2012, MOl. Pharm. vol. 9: 2049-2062.*
Baker et al., 2014, Curr. Opin. Rheum. vol. 26: 219-227.*
Fischer, Stefan et al. "The Preservation of Phenotype and Functionality of Dendritic Cells Upon Phagocytosis of Polyelectrolyte-coated PLGA Microparticles,"*Biomaterials*, 2007, 28(6): 994-1004.
Hubbell, Jeffrey A et al. "Materials Engineering for Immunomodulation," *Nature*, 2009, 462(7272): 449-460.
Jhunjhunwala et al., "Delivery of Rapamycin to Dendritic Cells Using Degradable Microparticles", *Journal of Control Release*, Oct. 26, 2008, 133(3): 191-197.
Keselowsky et al., "Multifunctional dendritic cell-targeting polymeric microparticles: Engineering new vaccines for type 1 diabetes", Jan. 1, 2011, *Human Vaccines*, 7(1): 37-44.

* cited by examiner

*Primary Examiner* — Amy E Juedes
(74) *Attorney, Agent, or Firm* — Saliwanchik, Lloyd & Eisenschenk

(57) ABSTRACT

The present invention provides antigen-specific, tolerance-inducing microparticles for the targeted delivery of therapeutic agents to immune cells. In addition, the present invention allows for sustained release of therapeutic agents for a prolonged period of time. Also provided are therapeutic uses of the present invention for the prevention and/or treatment of immune diseases and autoimmune disorders. In a specific embodiment, the present invention provides treatment for type 1 diabetes.

2 Claims, 12 Drawing Sheets

ANTIGEN-SPECIFIC, TOLERANCE-INDUCING MICROPARTICLES AND USES THEREOF

CROSS REFERENCE TO A RELATED APPLICATION

This application is a National Stage Application of International Application Number PCT/US2011/057478, filed Oct. 24, 2011; which claims priority to U.S. Provisional Application No. 61/405,999, filed Oct. 22, 2010, which are incorporated herein by reference in their entirety.

This invention was made with government support under Grant No. DK091658 awarded by the National Institutes of Health. The government has certain rights in the invention.

BACKGROUND OF INVENTION

Autoimmune diseases are frequently associated with a reduction in the number and function of regulatory T cells ($T_{reg}$s). These cells are known to suppress the levels of physiologic auto-reactive T cells. When the levels of auto-reactive T cells are elevated pathological destruction of desirable cells can result. For instance, type 1 diabetes is characterized by T-cell mediated destruction of insulin-producing β-cells.

Dendritic cells (DCs) play a critical role in the maintenance of peripheral tolerance. DCs promote $T_{reg}$ induction, thereby suppressing excessive immune responses. Dendritic cell-based vaccines have been demonstrated to promote tolerance through antigen-presenting cells (APCs). APCs process and present self-peptides in a tolerogenic manner to T-cells, and induce $T_{reg}$ proliferation. Apoptotic cells express surface ligands recognized by APCs via surface molecules such as the phosphatidyl serine (PS) receptor, CD 47, CD 36, and $α_vβ_3$. Recent studies imply that these receptors could inhibit DC maturation and induce tolerance.

The present use of dendritic cell-based DCs vaccines, however, suffers from several limitations. For instance, the present approach requires ex-vivo manipulation of patients' cells, which can adversely affect patient safety, and is associated with high cost. In addition, the present dendritic cell-based DCs vaccine compositions have suboptimal ex vivo stability.

Thus, there is a need for developing alternative vaccine compositions that have improved stability and shelf-life. In addition, there is a need for developing vaccine compositions that are effectively delivered to target cells. As will be clear from the disclosure that follows, these and other benefits are provided by the present invention.

BRIEF SUMMARY

The present invention provides antigen-specific, tolerance-inducing microparticles for targeted delivery to immune system cells.

In one embodiment, the present invention provides a microparticle that facilitates targeted delivery of compounds to immune cells of interest, wherein the microparticle comprises a polymeric matrix, an antigen (which includes, for example, auto-antigens and allergens), and a therapeutic agent of interest, wherein the antigen and the therapeutic agent are encapsulated in the polymeric matrix. In one embodiment, the outer surface of the microparticle comprises one or more molecules (such as ligands or antibodies) that are recognized by the immune cells. In one specific embodiment, the microparticles of the present invention target immature dendritic cells (DCs) and induce tolerance in an antigen-specific manner. Advantageously, the microparticles of the present invention specifically target immune cells, leading to intracellular phagocytosis or in-situ localization of microparticles; induce immunological antigen-specific tolerance, and produce tolerogenic DCs (tDCs) and $T_{reg}$s; and result in antigen presentation by immune cells such as DCs and antigen-specific immunosuppression.

In one embodiment, microparticles of the present invention are surface-modified with antibodies that allow them to effectively target DCs. In one embodiment, the microparticles are loaded with one or more therapeutic agents such as immunomodulatory factors (e.g., vitamin D3, TGF-β1, GM-CSF, or rapamycin). Advantageously, certain microparticles of the present invention generate tolerogenic DCs, and induce Foxp3$^+$ $T_{reg}$ cells, and, thus, are useful in the prevention and treatment of type 1 diabetes (T1D).

The present invention further provides methods for the prevention and/or treatment of autoimmune diseases, allergenic reactions, transplant rejection, chronic inflammation, and other diseases in which induction of specific tolerance is beneficial. Preferably, the method comprises administering, to a subject in need of such treatment, an effective amount of microparticles or a composition of the present invention. In a specific embodiment, the present invention provides treatments for type 1 diabetes.

BRIEF DESCRIPTION OF DRAWINGS

FIG. 7A shows 2.3 μm diameter, phagocytosable microparticles loaded with therapeutic agents. The size of the microparticles is determined by dynamic light scattering analysis. FIG. 7B shows that TGF-β1 (62±5% loading efficiency) is loaded into non-phagocytosable, 35 μm diameter microparticles (shown is rhodamine-loaded). FIG. 7C shows the encapsulation efficiencies of vitamin D3- and TGF-β1-loaded microparticles expressed as percent of theoretical maximum loading.

FIG. 8A shows surface modification with DC-targeting ligands selected from anti-CD 11c antibody, anti-Dec 205 antibody, or P-D2 peptide increases uptake of microparticles by DCs. Microparticles with tethered RGD peptide and PEG are included for comparison. FIG. 8B is a confocal microscopy image showing phagocytosis of fluorophore-loaded microparticles. FIG. 8C shows that P-D2 modified microparticles do not activate DCs when compared to blank microparticles, as determined by cytokine staining for IL-10 and IL-12. Immature DCs (iDCs) and LPS-matured DCs (LPS) are included for comparison. FIG. 8D shows that the surface-modified microparticles have negligible toxic effects on dendritic cells.

DETAILED DISCLOSURE

Figure 1:
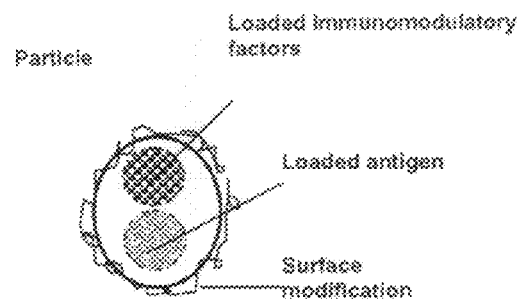
FIG. 1 illustrates a specific embodiment of the microparticle (MP) of the present invention.

The present invention provides antigen-specific, tolerance-inducing microparticles and therapeutic compositions comprising the microparticles. Advantageously, the present invention allows for the targeted delivery of therapeutic agents to immune cells. In addition, in certain embodiments, the present invention facilitates sustained release of therapeutic agents. Advantageously, the microparticle delivery system of the present invention has antigen-specificity and ex vivo stability.

In one embodiment, the invention provides a micorparticle for targeted delivery of one or more antigens along with immunomodulatory molecules to antigen-presenting cells (e.g., dendritic cells or macrophages). Particles fabricated using biodegradable materials can be loaded with hydrophobic and/or hydrophilic molecules. Additionally, vaccine particles can be targeted to specific antigen-presenting cells through particle surface modification. Delivered immunomodulatory molecules (e.g., transforming growth factor beta 1, rapamycin, vitamin D, and retinoic acid) can provide immunosuppressant/tolerogenic conditioning of antigen-presenting cells along with delivering an antigen depot for antigen-presenting cells to internalize and present to lymphocytes. Vaccine particles thus modulate antigen-presenting cell function to effect specific tolerance, suitable for applications such as for treatment of autoimmune disorders (e.g., type 1 diabetes), organ/tissue/cell transplantation or tissue engineered constructs.

Also provided are therapeutic uses of the present invention for the prevention and/or treatment of immune system disorders, including, autoimmune diseases. In a specific embodiment, the present invention provides treatments for type 1 diabetes.

Antigen-Specific Tolerogenic Compositions

In one aspect, the present invention provides therapeutic compositions that induce immune tolerance in an antigen-specific manner. In preferred embodiments, the composition comprises microparticles that target immune cells of interest, wherein the microparticle is made of biocompatible material, is surface-conjugated with ligands targeting the immune cells of interest, and encapsulates therein a therapeutic agent and an antigen(which, in certain embodiments is an auto-antigen and/or allergen). In one specific embodiment, the microparticles of the present invention target immature dendritic cells, release the encapsulated components in a timed fashion, and induce tolerance in an antigen-specific manner. The therapeutic composition can be formulated into a vaccine against autoimmune diseases, allergy, transplant rejection, chronic inflammation, and/or other diseases and conditions in which induction of specific tolerance would be beneficial.

Preferably, the microparticle matrix is made of, primarily, substantially biologically inert or biologically compatible materials. The terms "inert," "biologically inert" or "biologically compatible," as used herein, refer to a substance or material that, after the normal healing period when administered into living tissues, does not elicit substantially adverse biochemical, allergic, or unwanted immune responses.

Preferably, the present microparticle matrix is biodegradable. The term "biodegradable," as used herein, refers to the ability of materials to be broken down by normal chemical, biochemical and/or physical processes such as erosion, dissolution, corrosion, degradation, hydrolysis, abrasion, etc, and their combinations.

Biocompatible materials useful for making the microparticles include, but are not limited to, bio-degradable polymeric materials including, but not limited to, hydrogels, collagen, alginate, poly(glycolide) (PGA), poly(L-lactide) (PLA), poly(lactide-co-glycolide) (PLGA), polyethylene glycol (PEG), polyesters, polyanhydrides, polyorthoesters, polyamides; non-polymeric biodegradable ceramic materials including, but not limited to, calcium phosphate, hydroxyapatite, tricalcium phosphate; and combinations thereof. In a preferred embodiment, microparticles are fabricated from poly(lactic-co-glycolic acid) (PLGA), which is FDA approved for delivery of therapeutics.

Immune cells that can be targeted according to the present invention include, but are not limited to, dendritic cells, macrophages, lymphocytes, monocytes, neutrophils, mast cells, B cells, T cells, and T helper cells. In certain embodiments, professional antigen-presenting cells, such as dendritic cells, macrophages, T cells, and B cells, are targeted. In certain embodiments, dendritic cell and/or Treg cells are targeted.

In one embodiment, the outer surface of the microparticle comprises one or more surface ligands or surface antibodies that target specific immune cells. In certain embodiments, the surface ligands are chemicaly fixed, or covalently linked, to the microparticles. In one embodiment, the microparticles target dendritic cells. In a preferred embodiment, the microparticles specifically and selectively target immature dendritic cells, when compared to mature dendritic cells. Preferably, the surface ligands or antibodies also induce apoptotic and/or tolerance-inducing pathways in immune cells.

Exemplified surface ligands for dendritic cells include, but are not limited to, antibodies, aptamers and binding partners that bind specifically to cell surface ligands/receptors of dendritic cells, such as anti-CD 11 antibody and anti-Dec205 antibody; phosphatidyl serine (PS){PS receptor}; 4N1K {CD36/CD47}; PD2{CD11c}; P2 {CD11b}; RGD{$\alpha_v\beta_3$}; and CS1{$\alpha_4\beta_7$}. In one embodiment, the surface antibody is an anti-DEC-205 antibody, which recognizes dendritic cells. In a preferred embodiment, the microparticle matrix is surface modified with PD2 for targeting dendritic cells.

Therapeutic agents useful for encapsulation into the microparticles include, but are not limited to, immunomodulatory agents, anti-inflammatory, immunosuppressive and/or tolerogenic agents, agents that recruit the immune cells of interest, cytokines, and adjuvants, all of which are well known to those skilled in the field of immunology.

Immunomodulatory agents include, but are not limited to, vitamin D (e.g., vitamin $D_3$ and analog thereof), glucocorticoids, estrogens, rapamycin, and retinoic acid. Immunosuppressive, tolerogenic agents include, but are not limited to, anti-inflammatory cytokines such as IL-10, INF-gamma, and INF-lambda; and transforming growth factor beta 1 (TGF-β1). Therapeutic agents can be hydrophilic or hydrophobic substances.

A variety of agents that recruit or attract immune cells are also known. For example, chemoattractants that recruit dendritic cells include granulocyte macrophage colony stimulating factor (GM-CSF), granulocyte-colony stimulating factor (G-CSF), and macrophage colony-stimulating factor (M-CSF). Preferably, GM-CSF, which selectively attracts immature dendritic cells, is used in the present invention.

Anti-inflammatory or immunosuppressive agents useful according to the present invention also include nonsteroidal anti-inflammatory drugs (NSAIDs) such as aspirin, ibuprofen; naproxen, triterpinoids such as betulinic acid, bardoxolone methyl, and triterpenoid saponins.

Adjuvants useful in accordance with the present invention include, for example, CpG, poly I:C, and mPLA.

In certain specific embodiments, therapeutic agents useful according to the invention include T cell inhibitory agents such as cytotoxic T-lymphocyte antigen 4 (CTLA-4) and indoleamine 2,3 dioxygenase (IDO); Treg selective growth factors, such as IL-2, rapamycin, or a phosphodiesterase 3B (PDE3b) inhibitor, such as cilostamide; and agents that inhibit maturation of dendritic cells, such as vascular endothelial growth factor (VEGF) and transcription factor E2F1.

The microparticles of the present invention encapsulate therein antigens (including auto-antigens and/or allergens) to which the induction of specific tolerance would be beneficial. The choice of antigens depends on the particular autoimmune disease, allergic reactions, or inflammatory response to be prevented or treated, and can be determined by those skilled clinicians having the benefit of the current disclosure. Antigens that trigger a variety of hypersensitive immune responses have been characterized or can be identified via clinical testing. For instance, auto-antigens triggering type 1 diabetes include, but are not limited to, the 65 kDa isoform of glutamic acid decarboxylase (GAD), insulin, phosphatase-related 1A-2 molecule, epitopes of pancreatic beta cells and islet cells, etc. Auto-antigens triggering mutiple sclerosis include myelin basic protein. Common allergens include, but are not limited to, drugs, serum, peanuts, animal hair, pollens, and danders. In addition, to prevent transplant rejection, antigens can be derived from donor cells, tissues, or organs.

In one embodiment, in case of induction of dendritic cells with a tolerogenic phenotype, the therapeutic composition does not contain maturation stimuli such as prostaglandin E2.

FIG. 1 illustrates a specific embodiment of a microparticle of the present invention.

In one specific embodiment, the microparticle is phagocytosable by immune cells such as professional antigen-presenting cells. The phagocytosable microparticle comprises or encapsulates therein an antigen, auto-antigen, and/or allergen (e.g., a beta-cell specific autoantigen) and therapeutically effective immunomodulatory factors (e.g., vitamin D3 or rapamycin). Phagocytosis allows for endosomal release of encapsulated antigens and therapeutic agents from a polymeric matrix such as PLGA to intracellular targets. In one embodiment, the microparticles of the present invention generate both MHC-II-directed, as well as MHC-I-directed immune responses through cross-presentation.

In one embodiment, the microparticles of the present invention are not pinocytosable (nanoparticles are pinocytosable). The present microparticles effectively target phagocytes such as DCs. In one embodiment, the present microparticles do not target non-phagocytes.

In another specific embodiment, the microparticle is non-phagocytosable by immune cells such as professional antigen-presenting cells. In one embodiment, the non-phagocytosable microparticle comprises or encapsulates therein an agent for recruiting the immune cell of interest (e.g., GM-CSF) and an immunosuppressive agent (e.g., TGF-β1). The non-phagocytosable microparticle, localized to a site of interest, allows for sustained release of therapeutic agents in extracullular environment for a prolonged period such as, for example, a few days to several weeks. In one embodiment, the local delivery of immune-conditioning factors effects a tolerogenic DC phenotype, which promotes the induction of Treg cells and suppresses auto-reactive T-cells.

In certain embodiments, the microparticle phagocytosable by dendritic cells has a diameter in the range of 0.5 μm-10.0 μm, or any range therebetween, such as 0.5 μm-8.0 μm, 0.5 μm-5.0 μm, 0.5 μm-3.0 μm, 0.5 μm-2.0 μm, and 0.5 μm-1.0 μm. In certain embodiments, the microparticle has a diameter of about 1.0-3.0 μm.

In certain embodiments, the microparticle is non-phagocytosable by dendritic cells and has a diameter in the range of about 15.0 μm-200.0 μm, or any range therebetween, such as 15.0 μm-60.0 μm, 20.0 μm-50.0 μm, 20.0 μm-40.0 μm, 20.0 μm-35.0 μm, 15.0 μm-30.0 μm, 15.0 μm-25.0 μm, and 15.0 μm-20.0 μm.

The size of the microparticles can be optimized by those skilled in the art to achieve optimal delivery effects, depending on various parameters, such as for example, the cell type, the amount of therapeutics encapsulated, the site of delivery, and the host species.

In a further embodiment, the present invention provides a dual microparticle system comprising a mixture of microparticles phagocytosable by the immune cells of interest and microparticles non-phagocytosable by the immune cells of interest. In one embodiment, the dual microparticle system comprises a mixture of microparticles phagocytosable by dendritic cells and microparticles non-phagocytosable by dendritic cells.

Figure 6:
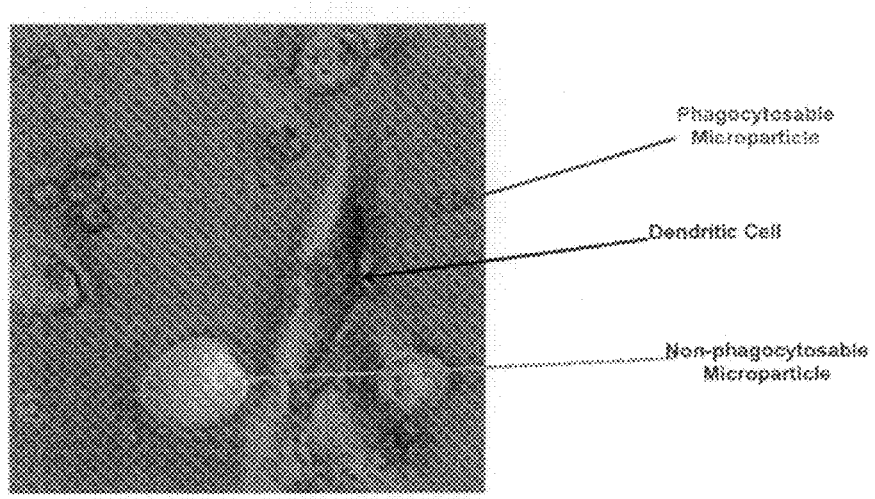
FIG. 6 shows two specifically-exemplified classes of injectable microparticles. The dual microparticle system comprises dendritic cell-targeting, phagocytosable microparticles and dendritic cell-targeting, non-phagocytosable microparticles. This dual system represents a rationally designed DC-modulating system to promote pro-tolerogenic DCs and antigen-specific immunosuppression.

FIG. 6 illustrates a specific embodiment of the dendritic-targeting, dual microparticle system of the present invention.

In another further embodiment, the present invention provides an injectable hydrogel composition, wherein the hydrogel comprises or encapsulates therein phagocytosable microparticles; an agent for recruiting the immune cell of interest (e.g., GM-CSF); and an immunosuppressive agent (e.g., TGF-β1); wherein the phagocytosable microparticles comprise or encapsulates therein an antigen (which can be an auto-antigen and/or allergen) (e.g., a beta-cell specific autoantigen) and an immunodulatory agent (e.g., vitamin D3, rapamycin). In one embodiment, the injectable, biodegradable hydrogel is fabricated via in situ gelling, and facilitates sustained-release of its ingredients for a prolong period of time (e.g., ~2 days).

In one embodiment, the therapeutic composition or the microparticle of the present invention does not contain any immune cells including, but not limited to, dendritic cells and Treg cells.

Induction of Antigen-Specific Immune Tolerance

In one aspect, the present invention provides therapeutic methods for inducing antigen-specific immune tolerance. Preferably, the method comprises administering, to a subject to which the induction of antigen-specific immune tolerance is needed, an effective amount of the microparticles and therapeutic compositions of the present invention. In a specific embodiment, the therapeutic composition of the present invention specifically targets dendritic cells, induces dendritic cells with a tolerogenic phenotype, promotes induction of Treg cells, and/or suppresses T cell proliferation.

The term "tolerance," as used herein, refers to a failure to respond, or a reduced response, to an antigen, including auto-antigens and allergens.

The term "tolerogenic" or "tolerance-inducing," as used herein, refers to a phenotype that induces tolerance to an antigen directly or indirectly, or is capable of silencing or down-regulating an adaptive immunological response to an antigen. Tolerogenic dendritic cells have a low ability to activate effector T cells, but have a high ability to induce and activate regulatory T cells. In one embodiment, tolerogenic dendritic cells typically have reduced MHCII, CD80, CD86 levels and express tolerogenic markers such as CD103 and indoleamine 2,3 dioxygenase.

Preferably, the microparticles of the present invention target immature dendritic cells, and do not target mature dendritic cells. Immature dendritic cells have a very dendritic morphology and have a low T cell activation potential. Immature dendritic cells undergo an irreversible maturation process upon activation of maturation stimuli. Mature dendritic cells have an enhanced ability to process antigens and activate T cells.

As demonstrated in the examples, the microparticles of the present invention can have improved DC-targeting specificity and increased uptake by DCs; result in functional antigen processing and presentation in DCs; facilitate the maintenance of immature DC phenotype, and prevent or delay the maturation and expression of tolerogenic DC markers (e.g., indoleamine 2,3 dioxygenase) following particle uptake; facilitate the suppression of allogeneic mixed lymphocyte reactions; and induce Foxp3$^+$ T$_{reg}$ cells.

In one embodiment, the administration of the microparticle composition results in downregulation of MHC-II, CD 86, and CD 80. In addition, microparticles surface modified with ligands 4N1K, RGD and/or CS1 show reduced T-cell proliferation in mixed-lymphocyte reaction tests compared to immature DC controls. In addition, the microparticles suppress auto-reactive T-cells through the induction of regulatory T-cells.

Specifically, in vivo data showed the administration of the present microparticle composition to late stage pre-diabetic, 12 week-old NOD mice, delays the onset of type 1 diabetes (T1D).

Advantageously, the present microparticle-encapsulated vaccine can be easily administered with simultaneous delivery of both prime and boost doses using time-release materials (e.g., poly lactide-co-glycolide).

Treatment of Immune Disorders and/or Autoimmune Diseases

The present invention provides methods for the prevention and/or treatment of autoimmune diseases, allergenic reactions, transplant rejection, chronic inflammation, and other diseases or disorders in which induction of specific tolerance would be beneficial. Preferably, the method comprises administering, to a subject, who has been diagnosed to be in need of such treatment, an effective amount of microparticles or a composition of the present invention.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, decreasing the number or frequency of relapse episodes, increasing latency between symptomatic episodes, or a combination thereof. Prevention, as used herein, does not require complete inhibition or elimination of symptoms.

The term "effective amount," as used herein, refers to an amount that is capable of treating a disease or condition or otherwise capable of producing an intended therapeutic effect. In one embodiment, an effective amount is a tolerogenic amount. For instance, an effective amount of an antigen is capable of inducing antigen-specific immune tolerance, but is incapable of generating an immunogenic reaction.

The term "subject," as used herein, describes an organism, including mammals such as primates, to which treatment with the compositions according to the present invention can be provided. Mammalian species that can benefit from the disclosed methods of treatment include, but are not limited to, primates such as apes, chimpanzees, orangutans, humans, monkeys; and non-primates such as dogs, cats, horses, cattle, pigs, sheep, goats, chickens, mice, rats, guinea pigs, and hamsters.

In certain embodiments, subjects treated in accordance with the present invention have been diagnosed with an autoimmune disease, allergy, chronic inflammation, and other disease or disorder in which induction of specific tolerance would be beneficial. In another embodiment, transplant recipients are treated with the present invention before, after, or at the time of the transplantation procedure.

In another embodiment, subjects treated in accordance with the present invention are diagnosed as susceptible to, or predisposed to, developing an autoimmune disease or other disease in which induction of specific tolerance would be beneficial. Autoimmune diseases are thought to have a strong genetic as well as environmental component. Certain individuals are regarded as genetically predisposed to autoimmunity. Many autoimmune diseases run in families. For example, many variants of the IDDM1 gene, such as DRB1 0401, DRB1 0402, DRB1 0405, DQA 0301, DQB1 0302 and DQB1 0201, are associated with higher risks of developing T1D. In addition, exposure to toxin and infection creates a higher risk of developing autoimmunity. Thus, predisposition or susceptibility to a particular type of autoimmune disease can be determined by a combination of factors, such as presence of a personal and family history of autoimmune disease, presence of genetic markers associated with autoimmunity, and/or living and/or working in conditions with a high chance of exposure to toxin or infection.

In one embodiment, the prevention and treatment method comprises, prior to administration of the microparticles and compositions of the invention, a step of diagnosing whether the subject has, or is predisposed to, an autoimmune disease or other disease or disorder in which induction of specific tolerance would be beneficial.

In one embodiment, the present invention can be used in the prevention and/or treatment of immune disorders and/or autoimmune diseases, particularly, type 1 diabetes. In certain embodiments, the present invention is useful to treat immune disorders and autoimmune diseases including, but not limited to, type 1 diabetes, rheumatoid arthritis, Crohn's disease, chronic inflammatory bowel diseases, multiple sclerosis (MS), oophoritis, graft-versus-host and transplant rejection, celiac disease, pemphigus vulgaris, and the prototype for autoimmune disease, systemic lupus erythematosus (SLE) and related disorders in which suppression of unwanted immune reaction is beneficial.

In certain embodiments, the present invention is useful to treat a disease or condition associated with immune disorders and autoimmune diseases. The diseases or conditions include, but are not limited to, asthma, allergies, rhinitis, chronic urticaria, and atopic dermatitis.

In addition, the present invention can be used in the prevention and/or treatment of chronic inflammation, transplant rejection, and allergenic reactions.

Further, the present invention can also be used to inhibit macrophage or T cell associated aspects of an immune response. The present invention can be used to inhibit macrophage or T cell activities including, but not limited to, macrophage antigen-presenting activity, macrophage-associated cytokine production, T cell cytokine production, T cell adhesion, and T cell proliferative activities. Thus, the present invention is also useful to suppress or inhibit humoral and/or cellular immune responses.

In one embodiment, DC-targeting microparticle formulations generate tolerogenic DCs and induce $T_{reg}$s, and, thus are useful for preventing and reversing T1D in NOD mice.

While in the experimental models of the present invention, type 1 diabetes was used as a therapeutic model of autoimmune diseases, it would be readily understood that the therapeutic benefits of the present invention extend beyond treatment of type 1 diabetes.

Screening Methods

Another aspect of the present invention provides a novel dendritic cell/microparticle cellular microarray for screening for tolerogenic immune cells such as dendritic cells, which serves to co-localize isolated populations of adherent DCs with surface-bound microparticles. This platform provides a means to screen large numbers of combinatorially-loaded microparticle formulations using only very few cells. The technology to screen using low cell numbers overcomes the barrier of the limited T1D patient-derived cell availability and takes a step toward personalized medicine. Thus, the present microparticle cellular microarray can be used for screening combinatorial particle formulations, using tolerogenic DC phenotypic markers as the criteria for optimization.

In one embodiment, the present invention provides a method for screening for therapeutic agents that induce an immune cell of interest with specific tolerance to an antigen, wherein the method comprises: a) providing microparticles comprising or encapsulating therein the antigen and a candidate therapeutic agent or a candidate combination of therapeutic agents, wherein the surface of the microparticle comprises a ligand that binds to the immune cell of interest;

b) contacting the immune cells with the microparticles;

c) determining whether the immune cells acquire a tolerogenic phenotype; and d) selecting the candidate therapeutic agent or the candidate combination of therapeutic agents if immune cells acquire a tolerogenic phenotype.

The immune cells of interest include antigen-presenting cells, such as dendritic cells and macrophages.

Candidate therapeutic agents include compounds of various chemical classes, such as organic or inorganic molecules, drugs, peptides or proteins, lipids, and nucleic acids; biological factors; cell extracts; and plant extracts, etc. For instance, the candidate therapeutic agents can be selected from immunomodulatory agents, immunosuppressive agents, tolerogenic agents, agents that recruit the immune cells of interest, adjuvants, cytokines, etc.

In one embodiment, a high throughput system is used to screen a plurality of candidate agents in vitro. Alternatively, the candidate agents can be delivered, via the microparticles, to animal subjects, thereby screening for the ability to induce specific tolerance in vivo.

The ability of inducing specific tolerance can be determined based on various parameters including, the presence of toleragenic markers (e.g., IDO), the induction of tolerogenic phenotypes, the ability of suppressing T cell proliferation, the ability of promoting induction of Treg cells, cytokine profiles, the induction of specific tolerance in vivo, and the prevention and/or treatment of autoimmune disease, allergy, chronic inflammation, transplant rejection, etc.

The parameters can be determined qualitatively or quantitatively, using standard methods such as immunofluorescent quantification, fluorescence activated cell sorting (FACS), flow cytometry, immunostaining, etc.

Formulations and Administration

The present invention provides for therapeutic or pharmaceutical compositions. In an embodiment, the composition comprises a therapeutically effective amount of a microparticle of the present invention and, optionally, a pharmaceutically acceptable carrier.

Suitable non-toxic pharmaceutically acceptable carriers for use with the agent will be apparent to those skilled in the art of pharmaceutical formulation. See, for example, *Remington's Pharmaceutical Sciences*, seventeenth edition, ed. Alfonso R. Gennaro, Mack Publishing Company, Easton, Pa. (1985).

The microparticles and therapeutic compositions of the present invention may be delivered to tissues, e.g., skin, muscle, organ, etc or other localized sites, e.g. lymph nodes, Peyer's patches, etc.

In one embodiment, the microparticles of the present invention are formulated into a vaccine composition for administration to subjects having certain risks of developing inflammatory and/or autoimmune-related disorders. In addition, the compositions of the present invention can be administered to a subject with existing symptoms of inflammatory and autoimmune-related disorders, and provides for customized vaccine schedules and compositions to prevent or minimize worsening of the diseases.

The therapeutic dosage range can be determined by one skilled in the art having the benefit of the current disclosure. Naturally, such therapeutic dosage ranges will vary with the size, species and physical condition of the patient, the severity of the patients medical condition, the particular dosage form employed, the route of administration and the like.

The composition can be administered in a single dose or in more than one dose over a period of time to confer the desired effect.

In a preferred embodiment, the microparticles of the present invention can be formulated for parenteral administration. The preparation of an aqueous composition that contains one or more agents, such as a genetic construct of the present invention, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Compositions comprising the microparticles of the present invention can be formulated into a composition in a neutral or salt form. Pharmaceutically acceptable salts include the acid addition salts and those formed with inorganic acids such as, for example, hydrochloric or phosphoric acids, or such organic acids as acetic, oxalic, tartaric, mandelic, and the like. Salts can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), dimethylsulfoxide (DMSO), suitable mixtures thereof, and vegetable oils. The proper fluidity can be maintained, for example, by the use of a coating, such as lecithin, by the maintenance of the required particle size in the case of dispersion and by the use of surfactants. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

The compositions of the present invention can be administered to the subject being treated by standard routes, including the topical, transdermal, intra-articular, parenteral (e.g., intravenous, intraperitoneal, intradermal, subcutaneous or intramuscular), intracranial, intracerebral, intraspinal, intravaginal, or intrauterine. Depending on the condition being treated, one route may be preferred over others, which can be determined by those skilled in the art. In preferred embodiments, the compositions of the present invention are formulated for parental administration. In another embodiment, the peptides and compositions of the present invention are formulated as a sustained-release formulation.

A further embodiment of the present invention provides for the administration of microparticles in combination with other pharmacological therapies. Combination therapies with other medicaments targeting similar or distinct disease mechanisms have advantages of greater efficacy and safety relative to respective monotherapies with either specific medicament.

When administering more than one, the administration of the agents can occur simultaneously or sequentially in time. The agents can be administered before and after one another, or at the same time. The methods also include co-administration with other drugs that are used to treat retinopathy or other diseases described herein.

EXAMPLES

Following are examples that illustrate procedures for practicing the invention. These examples should not be construed as limiting. All percentages are by weight and all solvent mixture proportions are by volume unless otherwise noted.

Example 1

Induction of Tolerogenic Dendritic Cells

This Example shows that the surface-modified microparticles of the present invention effectively target dendritic cells and induce dendridice cells with a "tolerogenic" phenotype.

Briefly, immature dendritic cells (iDCs) are obtained by culturing precursors isolated from bone marrow of C57BL/6j mouse in the presence of 20 ng/ml of growth factor GM-CSF for 10 days with half-media change every alternate day.

A 50:50 polymer composition of poly(d,l lactide-co-glycolide) (PLGA) (Lactel, AL, USA) is used to generate microparticles. Microparticles having a diameter of about several µm are formed using a standard oil-water solvent evaporation technique. The microparticles are surface-modified with ligands selected from CD11cAb, Dec-205Ab, Dec-205 Con, P-D2, P2, RGD, or REG. The uptake of microparticles by dendritic cells is determined by measuring total fluorescence of rhodamine-loaded microparticles prior to, and after, exposure to iDCs for 1 hr using a plate reader (excitation: 532 nm; emission: 585 nm). This assay is repeated for MΦs derived from bone marrow of BL/6 mice to compare the binding DC-specificity of the microparticles of the present invention to that of MΦs.

After 24 hours of cell culture with various surface-modified microparticles, cell culture supernatants are collected. The production of IL-12 cytokine subunit, IL-12p40, and IL-10 cytokine is analyzed using sandwich enzyme-linked immunosorbant assay (ELISA) kits (Becton Dickinson) according to manufacturer's directions.

To determine the level of expression of $L_{reg}$-inducing indoleamine 2,3 deoxygenase (IDO), dendritic cells are collected and stained with fluorescently-tagged anti-IDO antibodies following manufacturer's instructions and analyzed using flow cytometry. Additionally, T cell suppression is analyzed using standard allogenic MLR procedures followed by immuno-staining and flow cytometry.

Figure 2:
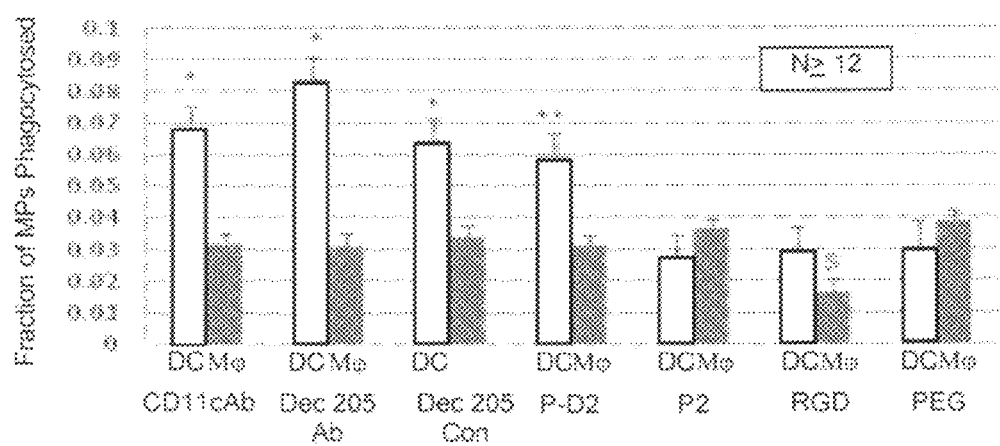
FIG. 2 shows a comparison of phagocytosis of the surface-modified microparticle by dendritic cells (DCs) (white) and Mϕ (black).
Figure 3:
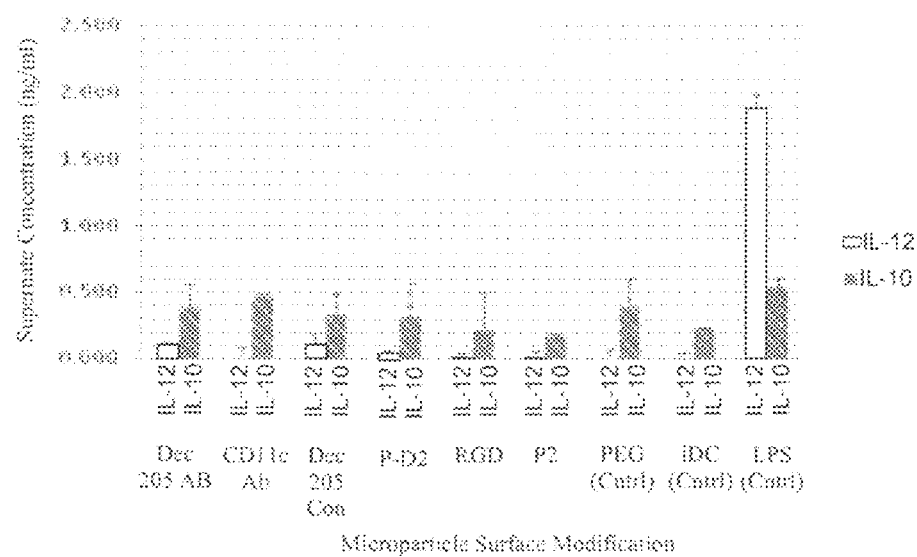
FIG. 3 shows the cytokine profile of DCs treated with surface-modified microparticles.
Figure 4:
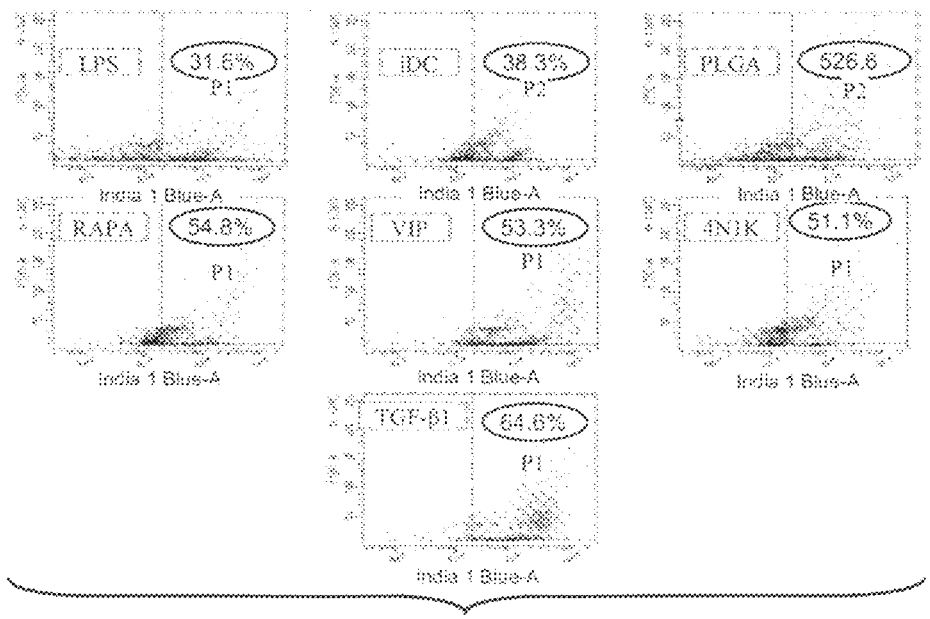
FIG. 4 shows results of the immunofluorescent quantification for determining the percentages of positively-stained DCs that are treated with the microparticles of the present invention.
Figure 5:
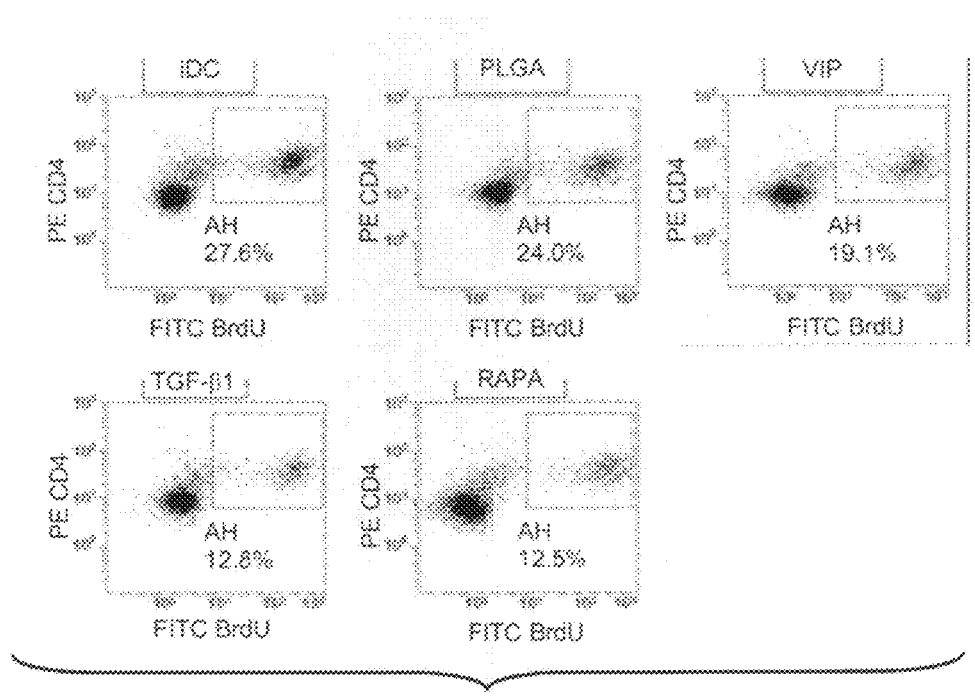
FIG. 5 shows the percentages of T cells positive for BrdU incorporation as determined by flow cytometry. DCs treated with immunosuppressive particles do not induce T cell proliferation in response to allogenic stimuli, when compared to controls (iDC, poly(lactic-co-glycolic acid (PLGA)).
Figure 7A:
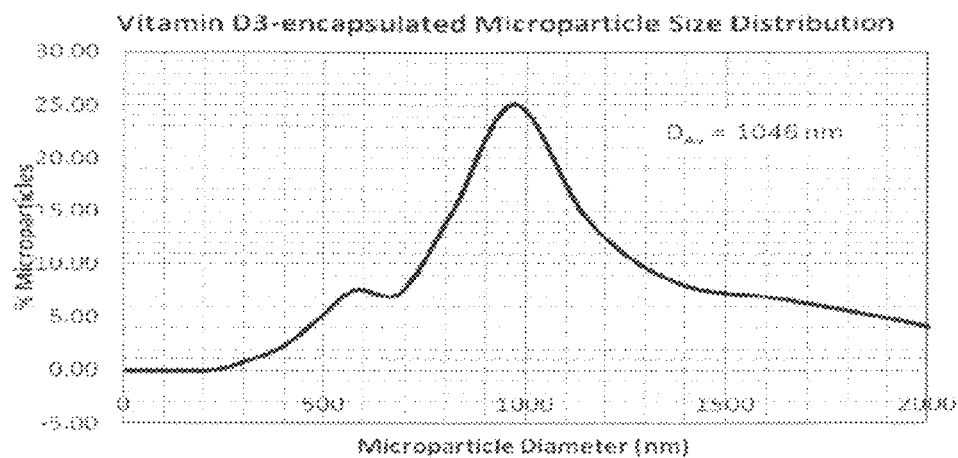
FIGS. 7A-C show microparticles (MPs) made of PLGA using water-oil-water solvent evaporation methods.
Figure 7B:
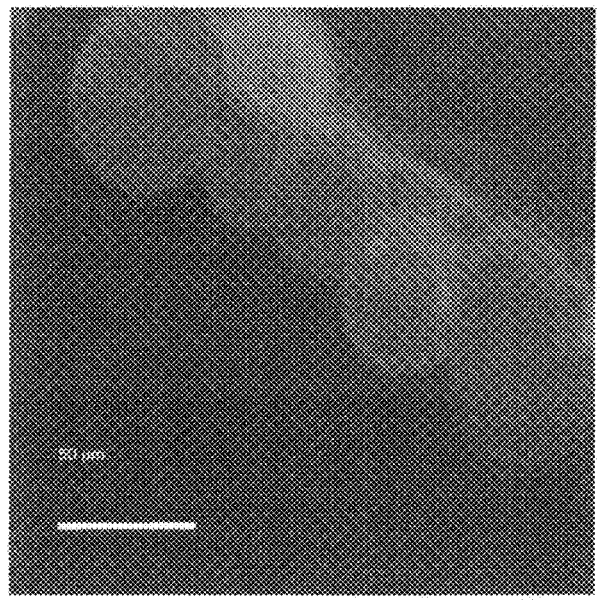
Figures 7C, 8A:
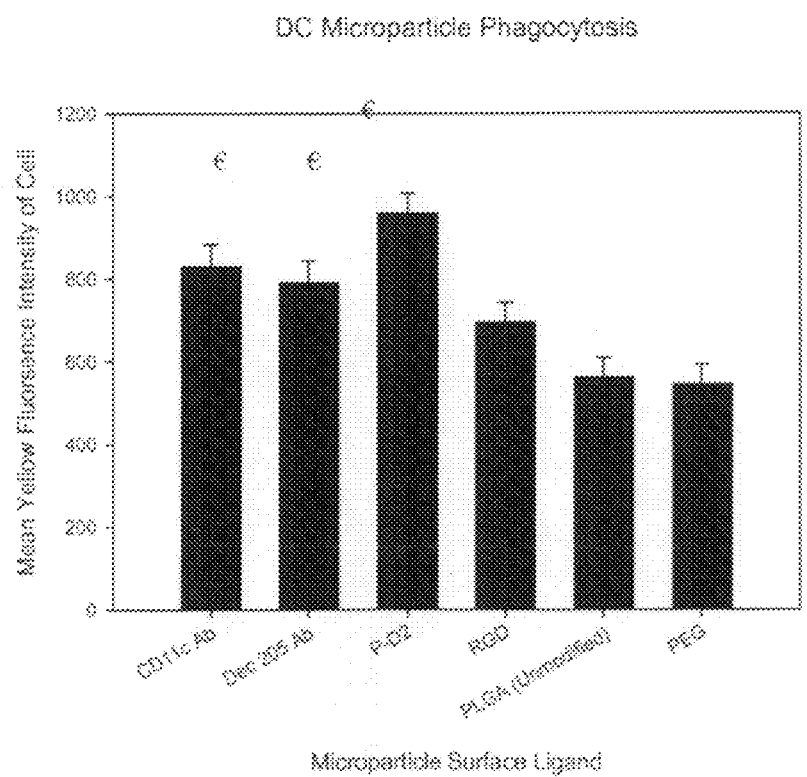
FIGS. 8A-D show that the microparticles of the present invention are DC-targeting, have satisfactory uptake properties, and are minimally activating.
Figure 8B:
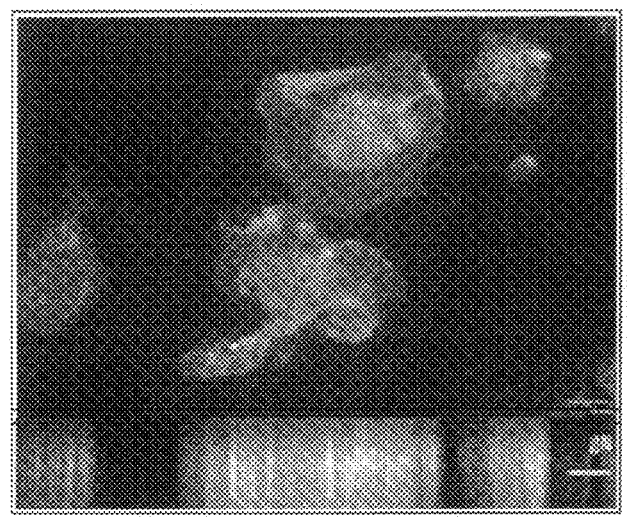
Figure 8C:
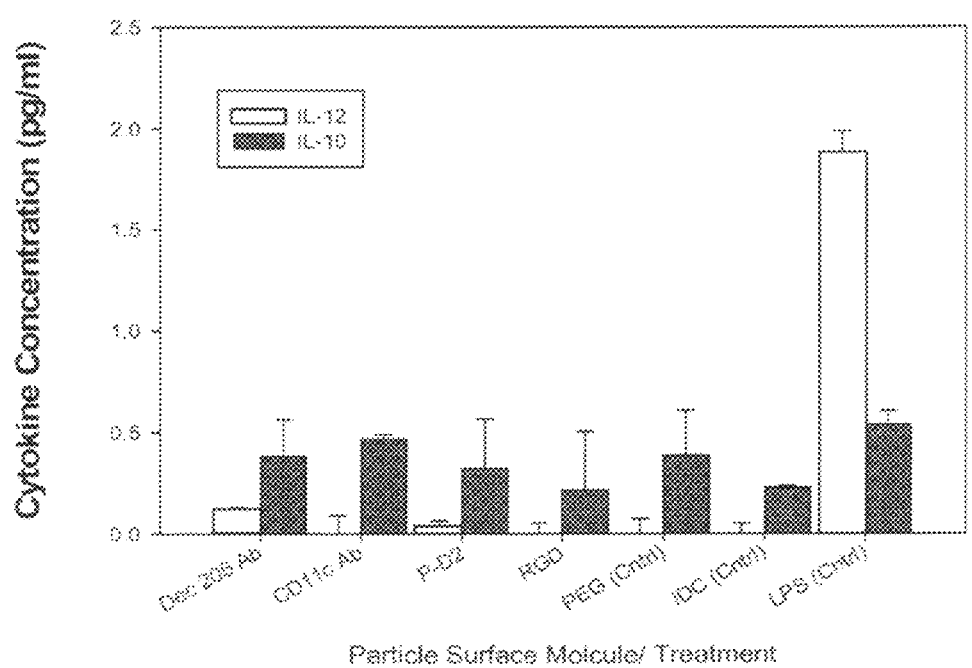
Figure 8D:
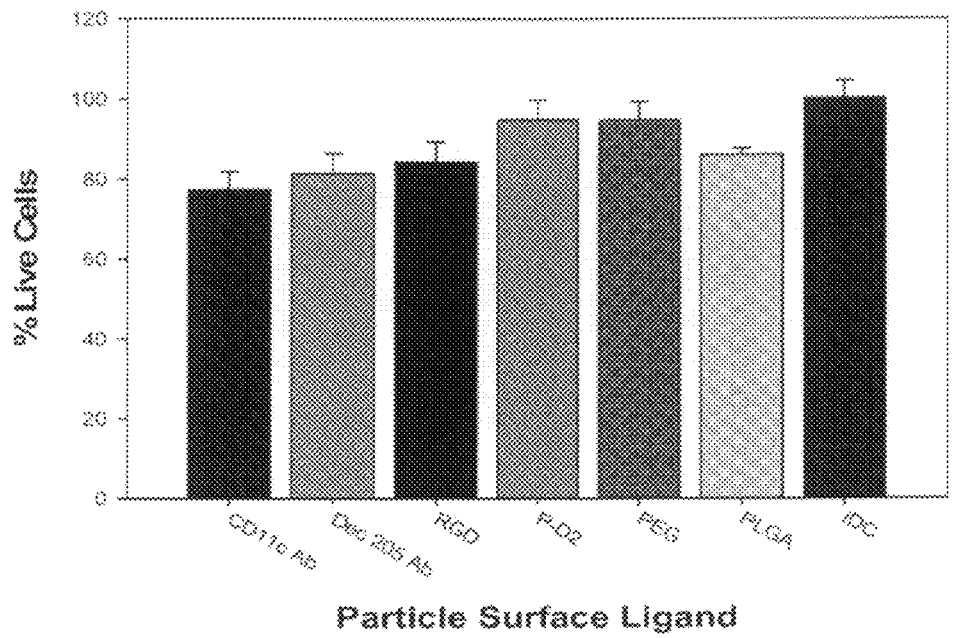

The results show that microspheres loaded with various ligands have differential levels of DC and Mφ uptake (FIG. 2, FIGS. 8A and B). Surface characterization of microparticles with ligands selected from CD11cAb, Dec205Ab, Dec205Con, P-D2, or P2 enhances uptake of microparticles by dendritic cells. In addition, cytokine analysis of dendritic cells treated with surface-modified microparticle show that the present microparticle formulations do not induce DC maturation (FIG. 3 and FIG. 8C). The results also show that drug-loaded microparticles of the present invention induce IDO expression in DCs (FIG. 4) and suppress T cell proliferation in MLR (FIG. 5). Also, the surface-modified microparticles have negligible toxic effects on dendritic cells (FIG. 8D).

The results demonstrate that the microparticle vaccine formulations of the present invention (a) target DCs in vitro for phagocytosis; (b) induce DCs with a "tolerogenic" phenotype, which have low MHC and co-stimulatory molecules, and produce immunosuppressive agents such as indoleamine 2,3 deoxygenase (IDO); and (c) reduce T-cell proliferation. Thus, the present microparticles, loaded with therapeutic agents, can be used as vaccine compositions for the prevention and treatment of a variety of immune disorders and autoimmune diseases.

Example 2

In Vivo Targeting and Trafficking of Surface-Modified Microparticles to Lymph Node Briefly, Did-loaded microparticles are surface modified via EDC chemistry with P-D2 pepitde (derived from ICAM-4). 1 mg of surface modified microparticles are injected into each footpad of C57BL/6 mice (n=2). Unmodified small- and large-diameter DiD-loaded microparticles are also injected into the footpads of respective mice as controls.

Three days after injection, popliteal lymph nodes are removed and processed in single cell suspensions, which are stained using CD11c (a dendritic cell marker) and F4/80 (macrophage marker) antibodies. Fluorescence activated cell sorting (FACS) analysis is performed to determine the percent of macrophages and DCs with DiD-loaded microparticles.

Figure 9:
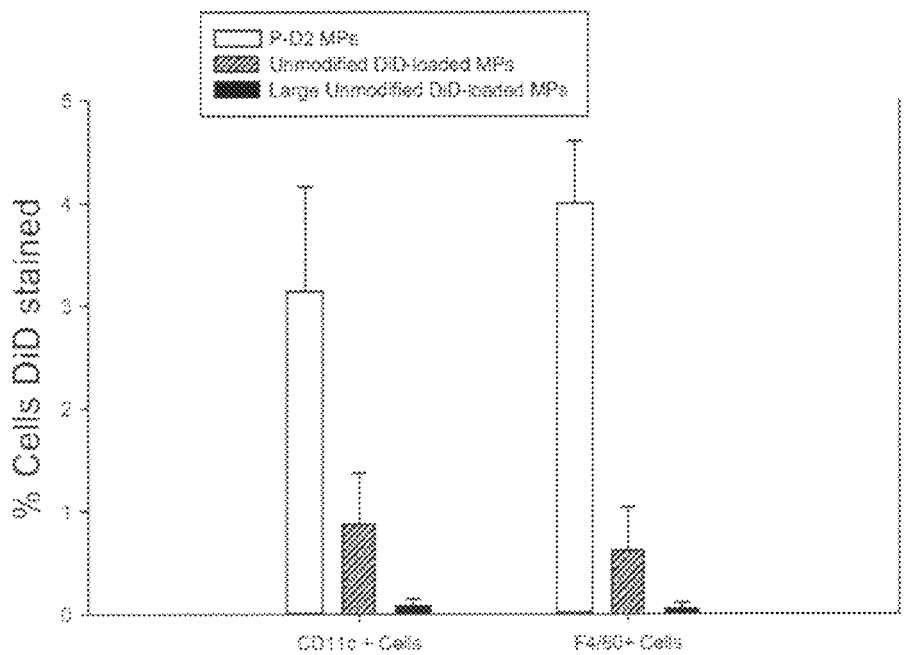
FIG. 9 shows that surface modification with P-D2 peptide greatly enhances the uptake and subsequent translocation of microparticles to the lymph node.

The results show that surface characterization with P-D2 peptide greatly enhances the uptake and subsequent translocation of microparticles to the lymph node (FIG. 9).

Example 3

Induction of Tolerogenic Dendritic Cells

Figure 10:
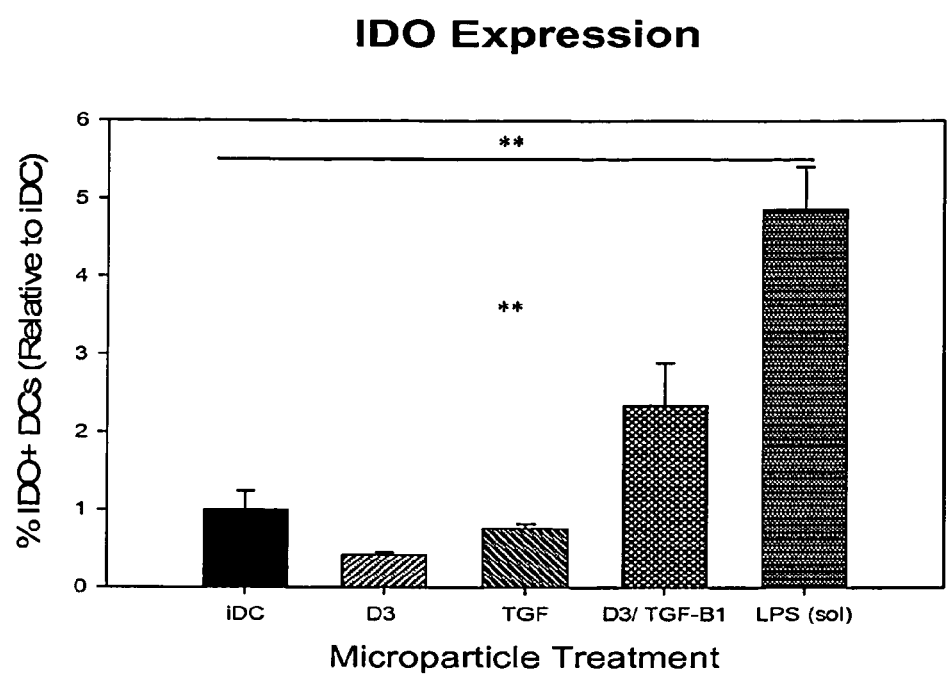
FIG. 10 shows that the microparticle formulations of the present invention promote production of tolerogenic dendritic cell marker indoleamine 2,3 dioxygenase (IDO).

This Examples shows that the microparticle formulations of the present invention induce tolerogenic dendritic cells, as shown by increased production of tolerogenic dendritic cell marker, indoleamine 2,3 dioxygenase (IDO). Briefly, DCs are incubated with MP encapsulated with vitamin D3 and/or TGF-β1 for 72 hours. After incubation, the DCs are fixed, permeablized, and immuno-stained for intracellular IDO. FIG. 9 is a graph showing flow cytometry data—forward scatter versus IDO. Controls of iDCs and blank PLGA MPS are included for comparison. The results show increased IDO expression in DCs incubated with MPs loaded with both vitamin D3 and TGF-β1 (FIG. 10).

Example 4

Antigen-Presentation by Dendritic Cells Treated with Antigen-Loaded Microparticles This Example shows that antigen encapsulated in the microparticles of the present invention is efficiently released, loaded, and presented by DCs to T-cells. Briefly, DCs are incubated with microparticles loaded with antigenic peptide 1040-55 (a BDC2.5 mimeotope) for 24 hours, then co-incubated with CD4+ T-cells isolated from BDC2.5 mice (All T-cells are engineered to carry the BDC2.5 T-cell receptor). T-cell stimulation is quantified by BrdU incorporation as a marker for T cell proliferation.

Figure 11A:
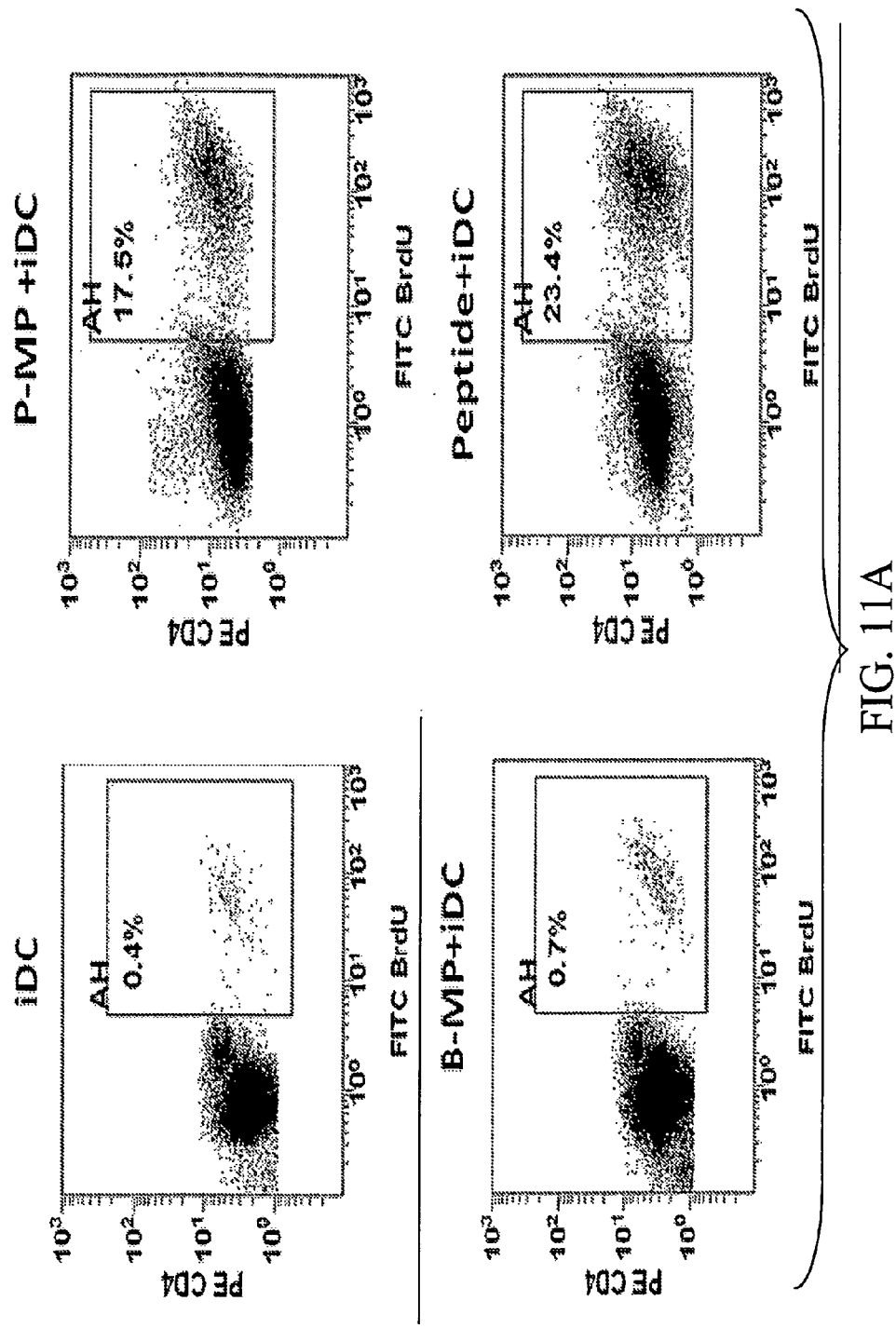
FIGS. 11A-B show that microparticle-encapsulated antigen is efficiently released, loaded, and presented by DCs to T-cells.
Figure 11B:
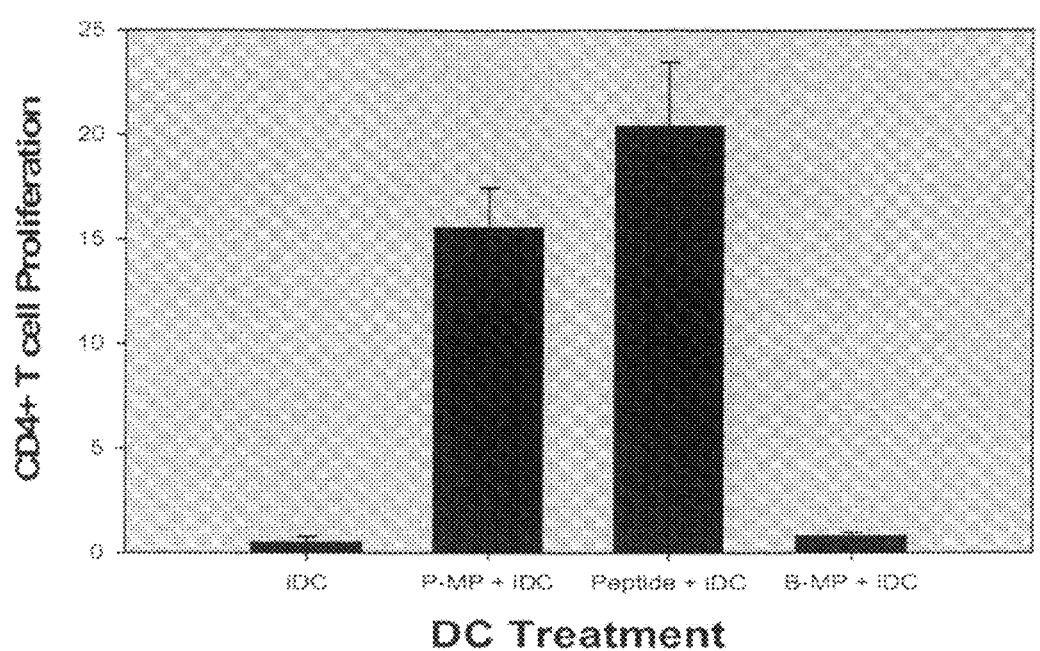
Figure 12A:
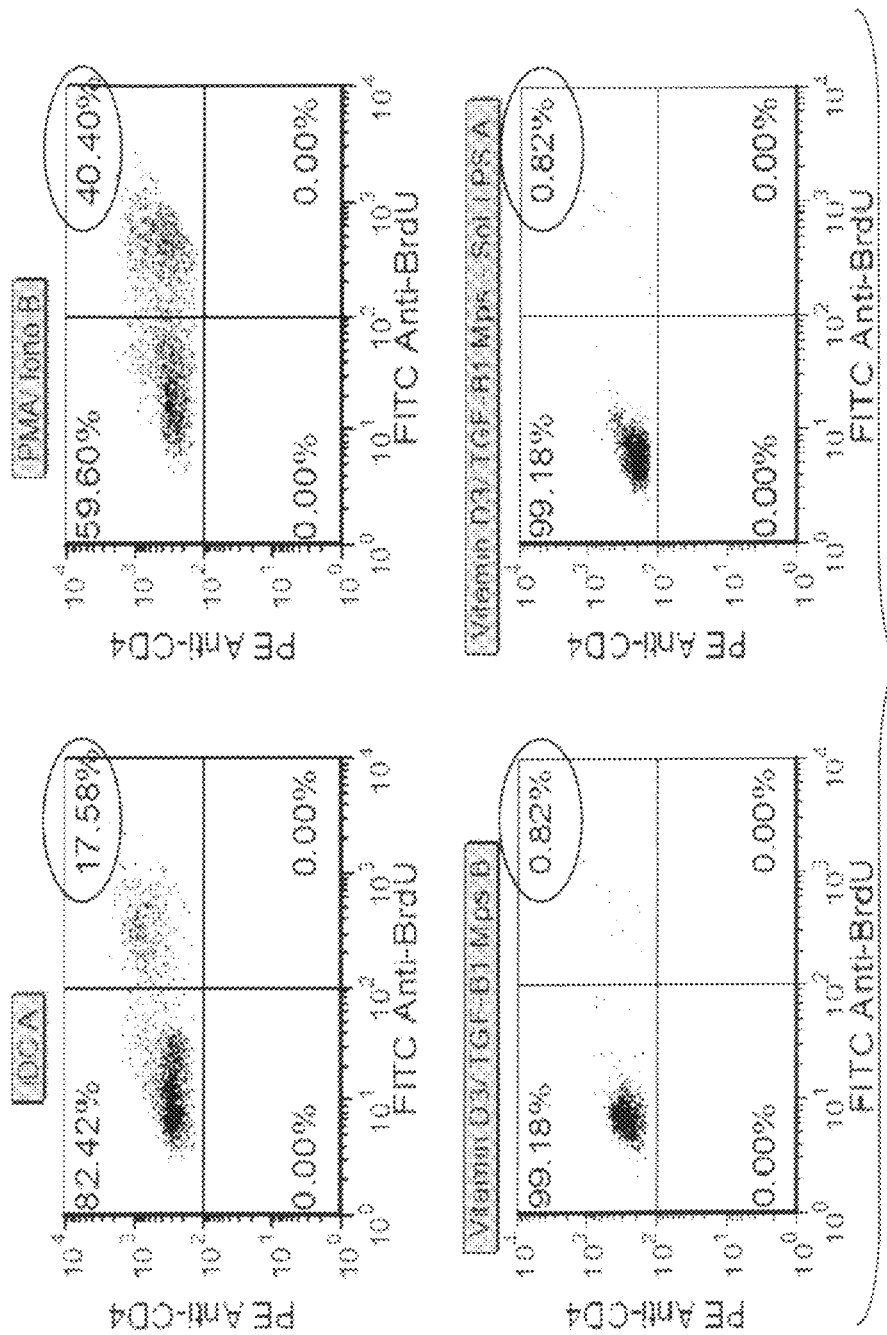
FIGS. 12A-B show that microparticle-treated DCs suppress allogenic T cell proliferation.
Figure 12B:
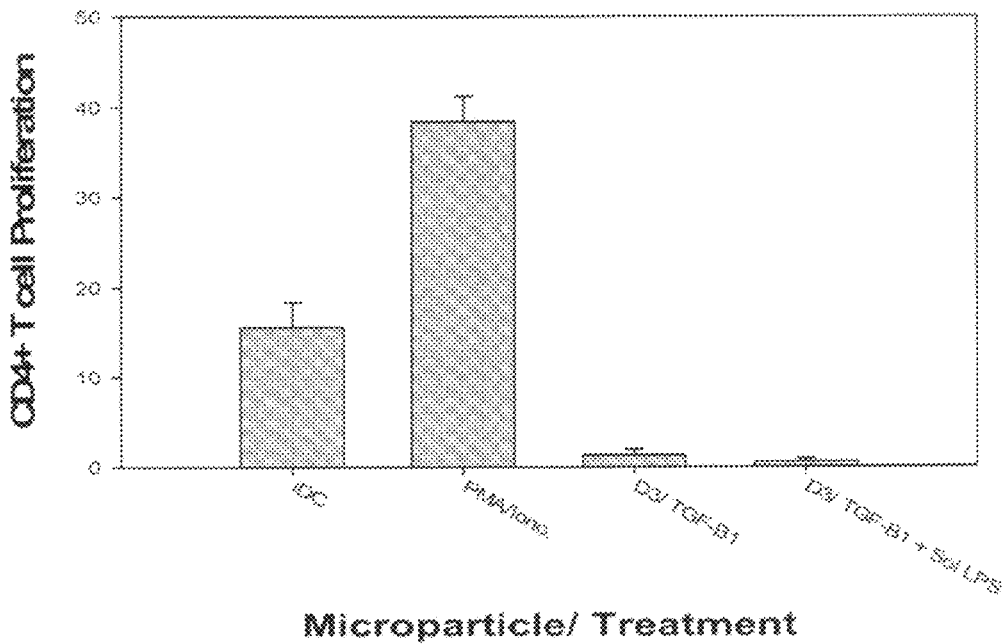
Figure 13:
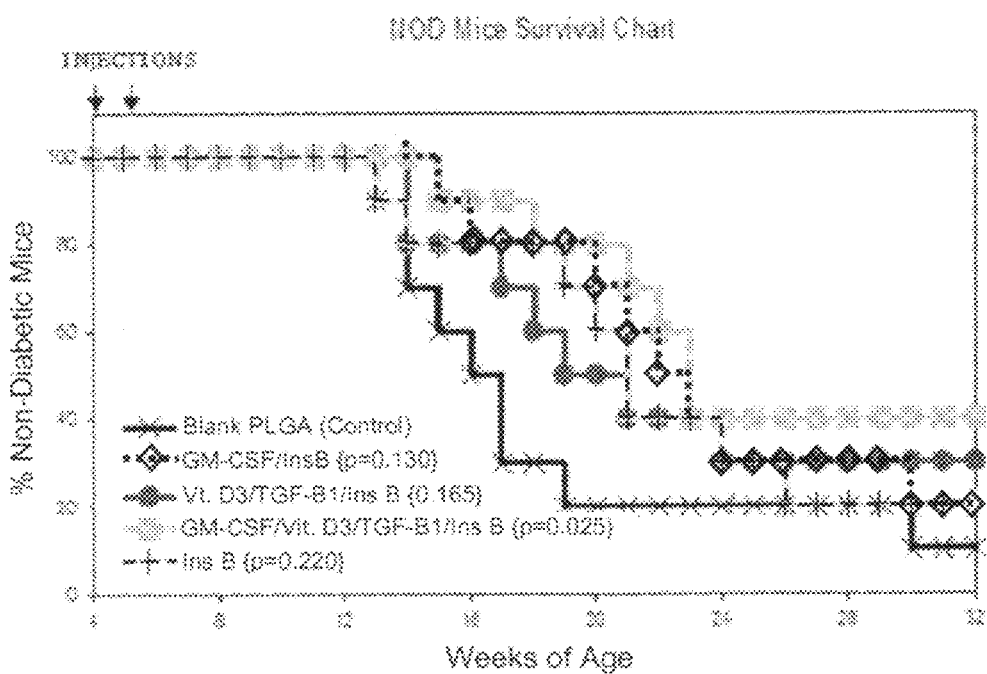
FIG. 13 shows that the antigen-specific, toleragenic microparticle formulations of the present invention prevent, delay, or reverse T1D in NOD mice.

The results, as shown in representative dot plot graphs (FIG. 11A) and the summary of pooled data in bar graph form (FIG. 11B), illustrate that DCs fed with the antigen peptide-loaded microparticles ("P-MP+iDC") are nearly as effective in presenting the peptide antigen as the positive control (DCs exogenously loaded with 1040-55 peptide: "Peptide+iDC"). Also shown are the negative controls of immature DCs ("iDC") and blank MPs ("B-MP+iDC").

Example 5

Suppression of Allogenic T Cell Proliferation by Microparticle-Treated Dendritic Cells This Examples show that formulations of MPs loaded with TGF-β1 and vitamin $D_3$ produce immunosuppressive effects. Briefly, dendritic cells are pre-incubated with the microparticle formulations for 72 hours. After pre-incubation, allogeneic CD4+T-cells are added to culture wells (ratio of 1:5, DC:T-cell), and this mixed lymphocyte reaction is cultured for 3 days. The cultures are pulsed with BrdU for 5 hours and then fixed, permeablized, immuno-stained for BrdU incorporation (for T cell proliferation) and CD4 (for T-cells). The cultures are also analyzed by flow cytometry.

The results show that the formulations of MPs loaded with TGF-β1 and vitamin D3 suppress allogenic T cell proliferation even in the presence of lipopolysaccharide ("Sol LPS"), when compared to levels of T-cell proliferation induced by iDCs or PMA/Ionomycin treatment (positive control).

Example 6

Prevention and Treatment of Type 1 Diabetes

This Example shows that the microparticle formulations of the present invention can be used to prevent and/or treat type 1 diabetes.

Briefly, a cohort of NOD mice are given injections of control and experimental microparticle formulations at 4 and 5 weeks of age. The experimental formulations of microparticles are loaded with a combination of GM-CSF and the insulin B peptide; a combination of vitamin D3, TGF-β1 and the insulin B peptide; and a combination of GM-CSF, vitamin D3, TGF-β1, and the insulin B peptide, respectively. The blood glucose levels of mice are monitored once weekly for the next 32 weeks after injection of microparticles. Once the blood glucose level is over 250 mg/dl for two consecutive days, diabetes is diagnosed and the mouse is sacrificed.

Statistical analysis of survival curves is performed in SYSTAT using Kaplan-Meier Non-parametric Survival analysis model. P values represent comparisons with the Blank PLGA treatment group.

The results show that the microparticle formulations of the present invention ("the experimental formulations") delay the onset of type 1 diabetes, when compared to controls. The microparticles loaded with vitamin $D_3$, GM-CSF, TGF-β1 and the insulin B peptide produce the greatest therapeutic effects. This indicates that the microparticle formulations of the present invention can be used to prevent, delay, or treat type 1 diabetes.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A dual microparticle system for targeting an antigen-presenting immune cell of interest in a subject and for reducing an immune response to an antigen, wherein the microparticle system is a liquid formulation that comprises:
microparticles that are phagocytosable by the antigen-presenting immune cell of interest, and microparticles that are non-phagocytosable by the antigen-presenting immune cell of interest, wherein the phagocytosable microparticles together comprise an antigen and at least one immunomodulatory agent selected from vitamin D3, vitamin D3 analog, glucocorticoid, estrogen, rapamycin, and retinoic acid; wherein the non-phagocytosable microparticles comprise at least one immunosuppressive tolerogenic agent selected from IL-10, TGF-β, and nonsteroidal anti-inflammatory drugs (NSAIDs), and an agent that recruits the antigen-presenting immune cell of interest selected from GM-CSF, G-CFS, and M-CSF; wherein the phagocytosable microparticle and the non-phagocytosable microparticles are made of PLGA.

2. The microparticle system of claim 1, wherein the phagocytosable microparticle has a diameter of 0.5 μm-5.0 μm and the non-phagocytosable microparticle has a diameter of 15.0 μm-50.0 μm.

* * * * *

UNITED STATES PATENT AND TRADEMARK OFFICE
CERTIFICATE OF CORRECTION

PATENT NO. : 10,016,371 B2
APPLICATION NO. : 13/880778
DATED : July 10, 2018
INVENTOR(S) : Benjamin George Keselowsky et al.

It is certified that error appears in the above-identified patent and that said Letters Patent is hereby corrected as shown below:

In the Specification

Column 2,
Line 34, "and Mγ" should read -- and Mφ --.

Column 3,
Lines 1-2, "anti-CD 11c" should read -- anti-CD11c --.

Column 4,
Line 62, "anti-CD 11" should read -- anti-CD11 --.

Column 10,
Line 62, "the patients" should read -- the patient's --.

Column 12,
Line 58, "$L_{reg}$-inducing" should read -- $T_{reg}$-inducing --.

Signed and Sealed this
Second Day of October, 2018

Andrei Iancu
*Director of the United States Patent and Trademark Office*